(12) United States Patent
McGhee

(10) Patent No.: US 7,820,734 B2
(45) Date of Patent: *Oct. 26, 2010

(54) ANTIMICROBIAL LUBRICIOUS COATING

(75) Inventor: Diane L. McGhee, Hazelwood, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 378 days.

This patent is subject to a terminal disclaimer.

(21) Appl. No.: 11/930,790

(22) Filed: Oct. 31, 2007

(65) Prior Publication Data

US 2008/0085949 A1 Apr. 10, 2008

Related U.S. Application Data

(63) Continuation-in-part of application No. 11/592,859, filed on Nov. 3, 2006, now Pat. No. 7,402,620, and a continuation-in-part of application No. 10/691,853, filed on Oct. 23, 2003, now Pat. No. 7,141,246, and a continuation-in-part of application No. 09/739,577, filed on Dec. 18, 2000, now Pat. No. 6,645,483, and a continuation-in-part of application No. 09/168,031, filed on Oct. 7, 1998, now abandoned.

(51) Int. Cl.
C09D 5/14 (2006.01)

(52) U.S. Cl. ............... 523/122; 523/105; 424/78.08; 424/78.31; 424/78.32; 424/78.35; 424/78.36; 424/78.38; 524/113; 524/233; 524/504; 604/264; 604/265; 106/15.05; 106/18.21; 106/461; 514/1; 514/461; 514/572

(58) Field of Classification Search .......... 523/122, 523/105; 424/405, 422, 423, 130.1, 280.1, 424/78.08, 78.31, 78.32, 78.35, 78.36, 78.37, 424/78.38; 524/113, 233, 504; 604/264, 604/265; 106/15.05, 18.321, 461; 514/1, 514/461, 572

See application file for complete search history.

(56) References Cited

U.S. PATENT DOCUMENTS

| | | |
|---|---|---|
| 3,939,049 A | 2/1976 | Ratner et al. |
| 3,975,350 A | 8/1976 | Hudgin et al. |
| 3,987,497 A | 10/1976 | Stoy et al. |
| 4,100,309 A | 7/1978 | Micklus et al. |
| 4,119,094 A | 10/1978 | Micklus et al. |
| 4,467,073 A | 8/1984 | Creasy |
| 4,769,013 A | 9/1988 | Lorenz et al. |
| 5,045,601 A | 9/1991 | Capelli et al. |
| 5,077,352 A | 12/1991 | Elton |
| 5,091,205 A | 2/1992 | Fan |
| 5,160,790 A | 11/1992 | Elton |
| 5,295,278 A | 3/1994 | Condon et al. |
| 5,295,978 A | 3/1994 | Fan et al. |
| 5,558,900 A | 9/1996 | Fan et al. |
| 6,458,867 B1 * | 10/2002 | Wang et al. ............ 523/105 |
| 6,645,483 B2 * | 11/2003 | McGhee ............ 424/78.08 |
| 7,141,246 B2 * | 11/2006 | McGhee ............ 424/405 |

FOREIGN PATENT DOCUMENTS

| | | |
|---|---|---|
| JP | 2-277458 | 11/1990 |
| JP | 4-227671 | 8/1992 |
| JP | 5-156203 | 6/1993 |
| JP | 5-505125 | 8/1993 |
| WO | WO 99/19004 | 4/1999 |
| WO | WO 00/44414 | 8/2000 |
| WO | WO 01/23015 | 4/2001 |
| WO | WO 02/058756 | 8/2002 |
| WO | WO 03/097727 | 11/2003 |
| WO | WO 2005/039665 | 5/2005 |

OTHER PUBLICATIONS

European International Search Report from Application No. EP 08 25 3563 mailed Mar. 25, 2009.

* cited by examiner

Primary Examiner—Kriellion A Sanders
(74) Attorney, Agent, or Firm—Thomas M. Johnston, Esq.

(57) ABSTRACT

The present disclosure provides lubricious antimicrobial coating vehicles for medical devices capable of reducing the coefficient of friction of such devices upon exposure thereof to moisture and imparting antimicrobial properties to said devices. The coating vehicle allows the introduction of a pharmacological additive having a release rate that is within acceptable pharmacokinetic criteria.

23 Claims, No Drawings

ANTIMICROBIAL LUBRICIOUS COATING

CROSS-REFERENCE TO RELATED APPLICATIONS

This application is a continuation-in-part of U.S. patent application Ser. No. 11/592,859 filed on Nov. 3, 2006 which, in turn, is a continuation of U.S. patent application Ser. No. 10/691,853 filed Oct. 23, 2003, now U.S. Pat. No. 7,141,246 which, in turn, is a continuation-in-part of U.S. application Ser. No. 09/739,577 filed Dec. 18, 2000, now U.S. Pat. No. 6,645,483 which, in turn, is a continuation-in-part of U.S. application Ser. No. 09/168,031 filed Oct. 7, 1998, now abandoned. The entire disclosures of each of the foregoing applications and patents are incorporated by reference herein.

BACKGROUND

1. Technical Field

The present disclosure relates to a lubricant coating for medical devices, and more particularly, to a hydrophilic polymeric coating which aids medical devices to become slippery when wetted. The lubricant coating of the present disclosure may be employed to reduce the coefficient of friction of catheters, arterial venous shunts, gastroenteric feed tubes, endotracheal tubes, urological catheters, wound care devices, and other medical implants or polymeric substrates. The coating of the present disclosure may also incorporate additive compounds such as antimicrobial agents that may be released in a pharmaceutically acceptable manner. Methods are also provided for the manufacture of the subject lubricant coating and for the application of the same to surfaces of medical devices.

2. Background of the Related Art

Known lubricant coatings applied to surfaces of medical devices include coatings of polyvinylpyrrolidone, polyurethane, acrylic polyester, vinyl resin, fluorocarbons, silicone rubber, and combinations of these substances. For example, Micklus et al., U.S. Pat. Nos. 4,100,309 and 4,119,094, relate to a hydrophilic coating of polyvinylpyrrolidone-polyurethane interpolymer formed using polyisocyanate. Ratner et al., U.S. Pat. No. 3,939,049, relates to a method of grafting hydrogels for lubrication to polymeric substrates using radiation. Hungton et al. U.S. Pat. No. 3,975,350, relates to hydrophilic polyurethane polymers for use as lubricants. Storey. et al. U.S. Pat. No. 3,987,497, relates to a tendon prosthesis having a lubricant hydrogel coating. Many known lubricious coatings are prone to various disadvantages when used in the medical field. Disadvantages of such known lubricants may include insufficiently low coefficient of friction, lack of permanence which may be a characteristic of silicone or fluorocarbon based coatings, slipperiness when dry as well as wet thus making handling difficult, utilization of hazardous solvents in the manufacture of the same and utilization of unstable reactive materials in the manufacture of the same. Lubricants produced for medical use from unstable reactive materials often require the coating solution to be prepared daily or more frequently to be useful and thereby increases waste and expense. Lubricants produced for medical use involving hazardous solvents are undesirable due to patient toxicity concerns and OSHA considerations. Also, lubricant coatings provided for inducing foreign devices into various areas of the body that are susceptible to infection and or thrombogenic reactions have failed to provide a pharmaceutically acceptable carrier for antimicrobial and anti-thrombogenic compounds.

In order to solve these and other potential disadvantages of known lubricants such as those of the above-cited patents, the entire disclosures of which are hereby incorporated by reference herein, a lubricant coating is needed that when wetted has sufficient lubricity to be useful in the medical device field such as for medical implants and the ability to incorporate within that coating antimicrobial compounds that can be released in a pharmaceutically acceptable manner. The lubricant coating must be capable of adhering to a wide variety of substrates and resist wet abrasion. It would also be desirable to have such a lubricant coating prepared from chemically stable and biocompatible solvents. Further, it would be advantageous to prepare such coating from components that are not health hazards.

SUMMARY

The present disclosure provides lubricious antimicrobial coatings for medical devices. In embodiments, a lubricant composition of the present disclosure may include an alcohol such as ethanol, denatured alcohol, and combinations thereof, an isocyanate-terminated prepolymer, a hydrophilic polymer other than an isocyanate-terminated prepolymer, and at least one antimicrobial agent. Isocyanate-terminated prepolymers may include polyoxyethylene-based isocyanate prepolymers, toluene diisocyanate-based prepolymers, isophorone diisocyanate-based prepolymers, hexamethylene isocyanate-terminated polyether prepolymers, and combinations thereof. Hydrophilic polymers other than an isocyanate-terminated prepolymer may include polyvinylpyrrolidone, polyvinyl alcohol, polyacrylic acid, polyethylene oxide, and combinations thereof. Suitable antimicrobial agents include biguanides, biguanide salts, silver, silver salts, aminoglycosides, quinolones, penicillins, cephalosporins, and combinations thereof. In embodiments, the coating may be placed in a solvent and applied as a solution.

Methods for producing these compositions are also provided. In embodiments, a method for producing a composition of the present disclosure may include contacting an alcohol selected such as ethanol, denatured alcohol, and combinations thereof with an isocyanate-terminated prepolymer, a hydrophilic polymer other than an isocyanate-terminated prepolymer, and at least one antimicrobial agent, and recovering the lubricant composition.

Medical devices possessing coatings of the present disclosure are also provided. In embodiments, a medical device of the present disclosure may be at least partially coated with a lubricious composition including an alcohol such as ethanol, denatured alcohol, and combinations thereof, an isocyanate-terminated prepolymer, a hydrophilic polymer other than an isocyanate-terminated prepolymer, and at least one antimicrobial agent.

DETAILED DESCRIPTION

The lubricant coating of the present disclosure has been found particularly useful in lowering the coefficient of friction of medical devices such as indwelling thoracic catheters and other medical devices. The subject coating may be manufactured from a blend including an alcohol, a polymer to increase hydrophilicity and lubricity, and an isocyanate-terminated prepolymer. In embodiments the coating may also include an antimicrobial additive.

According to the present disclosure, the lubricious coating contains an alcohol such as ethanol, denatured alcohol, combinations thereof, and the like. In embodiments, the alcohol may be anhydrous or nearly anhydrous, for example from about 98% to about 100% water-free, in embodiments about 99.5% water-free. It has been found that the alcohol may impart greater solubility of certain isocyanate-terminated prepolymers in the coating composition. In some embodiments, the alcohol may be utilized in combination with other solvents within the purview of those skilled in the art including, but not limited to, dimethylformamide (DMF), tetrahydrofuran (THF), methylene chloride, cyclohexanone, combinations thereof, and the like.

In embodiments, denatured alcohol may be utilized. As is readily apparent to one skilled in the art, denatured alcohol, in general, is ethanol which has been rendered toxic or otherwise undrinkable by the addition of additives such as methanol, isopropanol, methyl ethyl ketone, methyl isobutyl ketone, naphtha, pyridine, petroleum spirit, ethyl acetate, hydrocarbon solvent, toluene, methyl isobutyl ketone, combinations of the foregoing, and the like. In embodiments, a suitable denatured alcohol which may be utilized in accordance with the present disclosure includes those commercially available from Ricca Chemical Company (Arlington, Tex.).

Isocyanate-terminated prepolymers that can be used in forming lubricant coating compositions according to the present disclosure include, but are not limited to, polyoxyethylene-based isocyanates such as a toluene or isophorone diisocyanate-based prepolymers such as, for example, those sold under the HYPOL® name by the Dow Chemical Company (Marietta, Ga.), or VIBRATHANE®, a 4,4-diphenylmethane-disocyanante (MDI) urethane prepolymer manufactured by Chemtura, Inc., or ADIPRENE®, a low-free toluene diisocyanate (TDI), manufactured by Chemtura, Inc.

It is contemplated within the scope of the disclosure that other isocyanate-terminated prepolymers within the purview of those skilled in the art may be used. These prepolymers include, but are not limited to, polytetramethylene ether glycol-diphenylmethane diisocyanate (MDI), polytetramethylene ether glycol toluene diisocyanate (TDI), polytetramethylene ether glycol isophorone diisocyanate, poly(1,4-oxybutylene) glycol diphenylmethane diisocyanate (MDI), poly(1,4-oxybutylene) glycol toluene diisocyanate (TDI), poly(1,4-oxybutylene) glycol isophorone diisocyanate, polyethylene glycol diphenylmethane diisocyanate (MDI), polyethylene glycol toluene diisocyanate (TDI), polyethylene glycol isophorone diisocyanate, polypropylene glycol diphenylmethane diisocyanate (MDI), polypropylene glycol toluene diisocyanate (TDI), polypropylene glycol isophorone diisocyanate, polycaprolactone diphenylmethane diisocyanate (MDI), polycaprolactone toluene diisocyanate (TDI), polycaprolactone isophorone diisocyanate, polyethylene adipate diphenylmethane diisocyanate (MDI), polyethylene adipate toluene diisocyanate (TDI), polyethylene adipate isophorone diisocyanate, polytetramethylene adipate diphenylmethane diisocyanate (MDI), polytetramethylene adipate toluene diisocyanate (TDI), polytetramethylene adipate isophorone diisocyanate, polyethylene-propylene adipate diphenylmethane diisocyanate (MDI), polyethylene-propylene adipate toluene, diisocyanate (TDI), or polyethylene-propylene adipate isophorone diisocyanate polyurethanes.

In embodiments, a hexamethylene diisocyanate (HDI) terminated prepolymer can be used. The HDI icocyanate-terminated prepolymers offer improvements in worker safety. Suitable HDI prepolymers that have been found useful in the coatings according to the present disclosure include, but are not limited to, ADIPRENE® LFH 749 from Chemtura, Inc. (Middlebury, Conn.). This prepolymer is a reaction product of a polyether with HDI. The isocyanate-terminated prepolymer, in embodiments a hexamethylene isocyanate-terminated polyether prepolymer, may have less than about 0.1% free HDI, which can be beneficial in the management and control of worker exposure to HDI. This relatively low free HDI reduces dermal toxicity that can be associated with other prior art isocyanate-terminated prepolymers.

It is contemplated within the scope of the disclosure that urethanes such as PELLETHANE®, an aromatic ether polyurethane manufactured by Dow Chemical, or HYDROTHANE®, manufactured by CardioTech International, can be used in addition to or currently with the isocyanate-terminated prepolymers to enhance binding strength of the lubricant coating of the present disclosure. It is contemplated within the scope of the disclosure that other urethanes within the purview of those skilled in the art may be used.

The urethane may increase the binding strength of the coating and help control the rate of release, thereby enabling the pharmacokinetics, of any antimicrobial or other pharmacological additives in the lubricant coating composition to be within acceptable pharmaceutical limits, and it may also covalently bind anti-thrombogenic additives to prevent systematic absorption. While different urethanes have different properties and may require different solvent systems, the durometer of the urethane should match the durometer of the medical device to be coated or the functionality of the medical device may become compromised.

Suitable hydrophilic polymers other than isocyanate-terminated prepolymers which may be utilized in forming the coatings of the present disclosure include, for example, polyvinylpyrrolidone, polyvinyl alcohol, polyacrylic acid, polyethylene oxide, derivatives thereof, combinations thereof, and the like, to increase hydrophilicity and lubricity of the resulting coating. In embodiments, a polyvinyl pyrrolidone (PVP) may be included in the coating composition of the present disclosure. Suitable PVPs may have a molecular weight from about 12000 to about 400000, in embodiments from about 50000 to about 360000, and include those sold as KOLLIDON® 90F by BASF Corporation.

Solvent selection and blend ratio are important to provide adequate solubility and inertness to the lubricant coating and additives. For example, antimicrobial additives, such as silver salts or antibiotics, may be uniformly suspended within the coating solution. These additives are released on contact with moisture, the rate of release and the lubricious properties of the coating are controlled by altering the ratio of urethane and PVP. For further examples of suitable polyisocyanates see Encyclopedia of Polymer Science and Technology, H. F. Mark, N. G. Gaylord and N. M. Bikeles (eds.) (1969) incorporated herein by reference.

In accordance with the present disclosure, incorporating an antimicrobial or antithrombogenic agent having pharmaceutically acceptable pharmacokinetic properties in the coating will not interfere with the lubricous nature of the coating.

Antimicrobial additives utilized within the present disclosure include the biguanides, especially chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver chloride, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampician, bacitracin, neomycin, chloramphenical, miconazole, tolnaftate, quinolones such as oxolinic acid, norfloxacin, nalidix acid, pefloxacin, enoxacin and ciprofloxacin, penicillins such as ampicillin, amoxicillin and piracil, cephalosporins, vancomycin, and combinations of any of the above antimicrobials.

In other embodiments, suitable biguanides which may be utilized as antimicrobial additives include hexamethylene biguanides, oligo-hexamethyl biguanides, and/or water-soluble polymers, e.g. polyhexamethylene biguanide (PHMB), or a suitable salt thereof. Any polymeric biguanide within the purview of those skilled in the art may be used herein. Polymeric biguanides are characterized in that they may possess at least one, in embodiments about 2 or more, biguanide moieties according to the following formula:

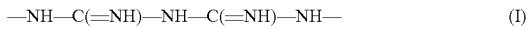

$$-NH-C(=NH)-NH-C(=NH)-NH- \qquad (I)$$

Polymeric biguanides useful herein may include oligo- or poly alkylene biguanides or salts thereof or mixtures thereof. Suitable salts include water-soluble salts with inorganic or organic acids, for example hydrochlorides, hydrobromides, borates, acetates, gluconates, sulfonates, maleates, ascorbates, stearates, tartrates or citrates. Examples of specific polymeric biguanides and salts thereof which may be utilized as antimicrobials include polyhexamethylene biguanide, polyhexamethylene biguanide hydrochloride, polyhexamethylene biguanide hydrobromide, polyhexamethylene biguanide borate, polyhexamethylene biguanide acetate, polyhexamethylene biguanide gluconate, polyhexamethylene biguanide sulfonate, polyhexamethylene biguanide maleate, polyhexamethylene biguanide ascorbate, polyhexamethylene biguanide stearate, polyhexamethylene biguanide tartrate, polyhexamethylene biguanide citrate, and combinations thereof.

In some embodiments, PHMB hydrochloride, PHMB stearate, and the like may be utilized. Polyhexamethylene biguanide hydrochloride, which has a molecular formula of $C_8H_{18}N_5Cl(C_8H_{18}N_5Cl)_n$, is a polymeric material with a molecular weight between about 1800 and about 2400 and is commercially available as COSMOCIL® CQ from ARCH® Biocides, a division of Arch Chemicals, Inc. (Norwalk, Conn.). PHMB hydrochloride is active against a wide range of microorganisms, it has very low mammalian toxicity, and it is chemically stable. Polyhexamethylene biguanide hydrochloride is also referred to as polyaminopropyl biguanide by the Cosmetic Toiletries and Fragrances Association (CTFA).

In embodiments, the lubricant coatings of the present disclosure may also include anti-thrombogenic additives. Such anti-thrombogenic additives are within the purview of those skilled in the art and include, but are not limited to, heparin. It is contemplated within the scope of the disclosure that modified forms of heparin may be used to ensure its biological activity and anti-thrombogenic properties. It is further contemplated that the urethane component may be modified to more readily accept the heparin or modified heparin molecule. According to the disclosure, anti-thrombogenic additives such as heparin may be blended into the polymeric component and/or the prepolymer component of the coating mixture. Without being bound to any particular theory, it is believed that the heparin molecule may be entrapped within the polymeric or prepolymer matrix.

Additionally, organic compounds derived from plants and herbs having desirable pharmacological properties can be utilized in the lubricant coating compositions of the present disclosure. Extracts of plants and herbs have been known to possess antimicrobial activity and their use has been shown to be safe for human and animal consumption. Extracts of such plants, known as phytochemicals, may be utilized for their antimicrobial properties. Some of these extracts, such as grapefruit seed extract, Tea Tree Oil, Myrtle Oil, combinations thereof, and others, can be incorporated into the lubricious coating vehicle and their antimicrobial properties released to the surrounding tissue in an efficacious manner.

In some illustrative embodiments of the present disclosure colorants, emulsifiers, surfactants, and color stabilizers that are well known within the art are added to the coating formulation. The colorants in the form of dyes or pigments aid in reducing shelf life discoloration or discoloration due to the effects of sterilization. The addition of emulsifiers and surfactants aid in suspension stability of the lubricous coating vehicle and surface wettability. Color stabilizers are sometimes added when the antimicrobial is a silver salt.

The release rate of pharmacological additives within the lubricious coating and the lubricity of the coating can be controlled by the adjustment of the concentration of the urethane prepolymer, i.e., the isocyanate-terminated prepolymer, and polymer such as PVP.

The lubricant coating vehicle of the present disclosure may generally be prepared by first obtaining a mixing vat in which to prepare the solution. In embodiments, the alcohol, antimicrobial, and PVP may first be combined to form a homogeneous solution. The amount of alcohol may be from about 50% by weight to about 98% by weight of the solution, in embodiments from about 85% by weight to about 96% by weight of the solution. The amount of antimicrobial may be from about 0.5% by weight to about 20% by weight of the solution, in embodiments from about 1% by weight to about 10% by weight of the solution. The amount of hydrophilic polymer, in embodiments PVP, may be from about 0.25% by weight to about 0.75% by weight of the solution, in embodiments from about 0.3% by weight to about 0.5% by weight of the solution. Finally, the amount of isocyanate-terminated prepolymer may then be added so that it is present in an amount from about 0.25% by weight to about 3% by weight of the solution, in embodiments from about 0.5% by weight to about 1% by weight of the solution.

Methods for forming the coating solution are within the purview of those skilled in the art. In embodiments, the alcohol, hydrophilic polymer and antimicrobial agent may first be combined in a mixing vessel or vat. Mixing may occur for a period of time from about 1 minute to about 2 hours, in embodiments from about 30 minutes to about 1 hour. In embodiments, the components may be added sequentially to help ensure homogeneous distribution.

At this point one may then add the isocyanate-terminated prepolymers to the mixture. The isocyanate-terminated prepolymer may be added and mixing allowed to continue for an additional period of time from about 5 minutes to about 2 hours, in embodiments from about 15 minutes to about 1 hour, to obtain a coating solution of the present disclosure.

The resulting coating solution should be clear. The coating solution is naturally moisture sensitive and will increase in viscosity if not tightly capped during storage. Any medical device that could benefit from a lubricious coating may be coated with the compositions of the present disclosure. In embodiments, such medical devices include, but are not limited to, catheters including indwelling thoracic catheters, arterial venous shunts, gastroenteric feed tubes, endotracheal tubes, urological catheters, wound dressings, and the like.

The medical device to be coated may be made of any biocompatible material. In embodiments, the medical device may be made of a polymeric material, a non-polymeric material, combinations thereof, and the like. For example, the medical device may be made of a polyester such as a MYLAR® polyester commercially available from DuPont. In other embodiments the medical device may be made of a material including polyvinyl chloride (PVC), silicone, polyurethane, combinations thereof, and the like.

Methods for applying the lubricant coating composition of the present disclosure to coat medical devices are also provided herein. Such methods may include, in embodiments, cleaning or washing, drying, dip coating, spraying, or similarly applying the lubricant coating composition, air drying or removal of excess lubricant, and optionally baking and packaging a medical device either before or after sterilization thereof.

For example, in embodiments, prior to coating medical devices with the present lubricant coating solution, the particular medical device, such as a catheter, may for optimal results be cleaned by first filling a container with 100% isopropanol. The medical device is then dip washed in the isopropanol for approximately 5 seconds and dried by forced air at approximately 50 to 90° C. to remove surface residual isopropanol and debris. The device should at this point be completely isopropanol free.

Methods for coating a medical device with a coating of the present disclosure are within the purview of those skilled in the art and include, for example, dipping, spraying, wiping, combinations thereof, and the like. For example, in embodiments where the coating solution is to be applied to a medical device made of a MYLAR® film or some other similar non-porous substrate, the coating may be applied by spraying. In other embodiments, including those where the medical device is made of a polymeric material, dipping may be utilized to apply a coating of the present disclosure to the medical device. In embodiments, where dipping is utilized to apply a coating of the present disclosure to a medical device, the medical device may be dip coated for a period of time of from about 1 second to about 5 minutes, in embodiments from about 5 seconds to about 2.5 minutes in the lubricant coating vehicle solution, and slowly removed from the solution vat at a rate of about 0.5 inches per second.

Once the coating solution has been applied, it may be useful, in embodiments, to heat the medical device with coating solution thereon to a temperature of from about 30° C. to about 70° C., in embodiments from about 37° C. to about 60° C., for a period of time from about 20 minutes to about 2 hours, in embodiments from about 30 minutes to about 90 minutes. After this heating has occurred any excess lubricant coating solution should have drained off. In embodiments, excess lubricant may also be removed using non-linting wicking agents. The coated medical devices may then optionally be baked in forced air ovens at from about 45° C. to about 65° C. +/−5° C. for a period of time from about 30 minutes to about 3 hours, in embodiments for about one hour, and then removed from the oven.

Curing temperature and time are dependent upon the specific alcohol, hydrophilic polymer, antimicrobial agent, and isocyanate-terminated prepolymers utilized in forming the coating solution of the present disclosure, as well as the amounts of these components in the coating solution of the present disclosure. Where the coating solution is utilized to coat a polymeric medical device, the diisocyanate of the isocyanate-terminated prepolymer may react with and become a part of the polymer structure of the medical device.

The medical devices coated in accordance with the present disclosure may be periodically checked for adequate transparency and to ensure that no undesirable odor is present.

In packaging the subject medical devices coated in accordance with the present disclosure, the devices should not be allowed to touch one another. This is especially true if the environment humidity is high, which could cause undesirable moisture absorption by the lubricant coating. To prevent or avoid such contact between the coated medical devices, each device may be packed in either paper, polyethylene tubing or the like depending on the shape of the particular device. If necessary, due to high atmospheric humidity, a desiccant may likewise be necessary in the packaging.

The coatings of the present disclosure adhere to a wide variety of substrates and resist wet abrasion. The subject lubricant coating is chemically stable and is biocompatible.

The present disclosure also provides a medical device whereby at least a portion thereof is coated with the subject lubricant coating, which is characterized as being able to achieve a wetted lubricity with a reduction of friction of more than about fifty percent, in embodiments from about 50 percent to about 90 percent, in other embodiments from about 65 percent to about 85 percent. In addition, while a MYLAR® film is by nature a non-adherent film, the addition of PVP may provide a synergistic effect in reducing the coefficient of friction of such a film or substrates made of similar materials, as well as their non-adherent properties. Moreover, PVP may also be utilized for additional beneficial effects in a wound care setting including, for example, its ability to aid in the elution of a pharmacological agent from a coating of the present disclosure.

Medical devices once coated with the lubricious coating vehicle of the present disclosure may be packaged and sterilized using an appropriate sterilization technique or may be sterilized and then packaged using an aseptic technique. Appropriate methods of sterilization and packaging are within the purview of those skilled in the art and include gamma radiation, electronic beam, ethylene oxide, and like methods. In embodiments, medical devices coated with the subject coating may be packaged and then sterilized using gamma radiation by cobalt 60 with 1 to 3 mrads, in embodiments about 2 mrads, in two independent exposure cycles for superior results.

Appropriate packaging for the subject coated medical devices includes metallic foil pouches such as aluminum foil pouches, polyethylene film, ethylene vinyl acetate film, polypropylene film, polyvinyl chloride film, TYVEK® and like packages within the purview of those skilled in the art. In embodiments, a suitable package may include an aluminum foil cover pouch with an ethylene vinyl acetate film inner liner to prevent moisture absorption by the coating.

It is contemplated within the scope of the present disclosure that some pharmaceutical additives may be light sensitive and therefore medical devices coated with such additives should be packaged in appropriate light packaging within the purview of those skilled in the art.

Methods of using the subject coated medical devices include removing the device from its packaging, applying moisture to the lubricated surface of the device and placing the device as necessary for a particular medical procedure.

It is seen therefore that the present lubricious coating vehicle for medical devices provides an effective wet abrasion resistant, low coefficient of friction coating for medical devices and a vehicle for delivering additives such as antimicrobials and other pharmacological active compounds. The lubricious coating vehicle, the method of making and using the lubricious coating vehicle, the coated medical devices and the method of using the coated medical devices as disclosed and described herein have specific advantages over heretofore known lubricants for medical devices. The subject lubricious coating vehicle resists wet abrasion, adheres to a variety of surfaces, has a decreased coefficient of friction only when wetted, is biocompatible, and is able to deliver pharmacological active agents with acceptable pharmacokinetic properties. Hence for these reasons, as well as others, it is seen that the present lubricious coating vehicle represents a significant advancement in the art which has substantial commercial significance.

Although the lubricious coating vehicle described in the illustrative embodiments herein include coatings pertaining to antimicrobial additives and the methods for ensuring that the pharmacokinetics are within efficacious ranges, it should be appreciated that additives within the lubricious coating vehicle could be other desirable pharmaceutical active compounds such as topical anesthetics, anti-inflammatory compounds both non-steroidal and steroidal, spermicidal compounds, or the like. Similarly, rather than the traditional pharmaceutical compounds the additives can be organic compounds with desired pharmacological effects.

Suitable methods for making and using the lubricant coating vehicle of the present disclosure are described in even greater detail in the following examples which are provided for purposes of further illustration. The following illustrative examples as described are not intended to be construed as limiting the scope of the present disclosure.

EXAMPLES

Example 1

An anti-microbial lubricious coating was prepared by blending at room temperature the following components in a mixing vat for approximately 1 hour until fully dissolved to form a crystal clear solution.

| Ingredient | % (wt) |
|---|---|
| Ethyl Alcohol | 97.25 |
| PVP | 0.25 |
| PHMB | 1.5 |
| Isocyanate-terminated prepolymer | 1 |

Wound care film samples made of MYLAR® film were dip coated in the above solution for about 10 seconds. After dipping, excessive coating was removed using non-linting wicking agents. The film samples were then oven cured at about 55° C. for about 35 minutes. The resultant coating was transparent and colorless with good bonding.

Example 2

An anti-microbial lubricious coating using a phyto-chemical was prepared by blending at room temperature the following components in a mixing vat for approximately 1 hour until fully dissolved to form a crystal clear solution.

| Ingredient | % (wt) |
|---|---|
| Ethyl Alcohol | 93.75 |
| PVP | 0.25 |
| Myrtle Oil/Tea Tree extract | 5 |
| Isocyanate-terminated prepolymer | 1 |

Wound care film samples made of MYLAR® film were dip coated in the above solution for about 10 seconds. After dipping, excessive coating was removed using wicking agents.

The film samples were then oven cured at about 55° C. for about 35 minutes. The resultant coating was transparent and colorless with good bonding.

Example 3

A lubricious coating vehicle, containing silver salts for use on medical devices, is prepared by blending at room temperature the following components in a mixing vat for approximately 60 minutes until fully dissolved to form a crystal clear to pale yellow solution. The order of combination of the ingredients is not imperative due to the lack of covalent bonding of the silver salt to the urethane. The release of the silver salt is regulated by PVP ratio adjustment due to entrapment/ionic bonding of the salt. Suitable silver salts include: Giltech Powders 01-07 (this is a water soluble glass silver salt produced by Giltech Ltd.); AlphaSan RC2000 (this is a zirconium/phosphate crystal produced by Milliken Chemical); SSD (silver sulfadiazine from Kendall); and silver chloride (obtained from Fisher Scientific).

A specific example formulated with SSD was as follows:

| Ingredient | % (wt) |
|---|---|
| Ethyl Alcohol | 96.75 |
| PVP | 0.25 |
| SSD | 2 |
| Isocyanate-terminated prepolymer | 1 |

The ingredients were mixed at room temperature in the above order. It was found that the PVP level should not exceed approximately 2.5%, as higher levels detrimentally affected coating adherence and silver release. The amount of silver complex added to the formula was determined by the overall percent of silver loading within the salt complex. The particle size of the silver complex was very important in that it may cause problems in coating adherence. That is, larger particle size yielded poor coating adherence and uniformity. SSD had a 30% silver loading with sulfadiazine making up the bulk.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, or material.

What is claimed is:

1. A lubricant composition comprising:
    an alcohol selected from the group consisting of ethanol, denatured alcohol, and combinations thereof;
    an isocyanate-terminated prepolymer;
    a hydrophilic polymer other than an isocyanate-terminated prepolymer; and
    at least one antimicrobial agent.

2. The composition of claim 1, wherein said isocyanate-terminated prepolymer is selected from the group consisting of polyoxyethylene-based isocyanate prepolymers, toluene diisocyanate-based prepolymers, isophorone diisocyanate-based prepolymers, hexamethylene isocyanate-terminated polyether prepolymers, and combinations thereof.

3. The composition of claim 1, wherein said hydrophilic polymer is selected from the group consisting of polyvinylpyrrolidone, polyvinyl alcohol, polyacrylic acid, polyethylene oxide, and combinations thereof.

4. The composition of claim 1, further comprising a solvent selected from the group consisting of dimethylformamide, tetrahydrofuran, methylene chloride, cyclohexanone, and combinations thereof.

5. The composition of claim 1, wherein the antimicrobial agent selected from the group consisting of biguanides, biguanide salts, silver, silver salts, aminoglycosides, quinolones, penicillins, cephalosporins, and combinations thereof.

6. The composition of claim 1, wherein the antimicrobial agent is selected from the group consisting of chlorhexidine, chlorhexidine acetate, chlorhexidine gluconate, chlorhexidine hydrochloride, chlorhexidine sulfate, hexamethylene biguanides, oligo-hexamethyl biguanides, silver acetate, silver benzoate, silver carbonate, silver chloride, silver iodate, silver iodide, silver lactate, silver laurate, silver nitrate, silver oxide, silver palmitate, silver protein, silver sulfadiazine, polymyxin, tetracycline, tobramycin, gentamicin, rifampician, bacitracin, neomycin, chloramphenical, miconazole, tolnaftate, oxolinic acid, norfloxacin, nalidix acid, pefloxacin, enoxacin, ciprofloxacin, ampicillin, amoxicillin, piracil, vancomycin, and combinations thereof.

7. The composition of claim 1, wherein the antimicrobial agent is selected from the group consisting of polyhexamethylene biguanide, polyhexamethylene biguanide hydrochloride, polyhexamethylene biguanide hydrobromide, polyhexamethylene biguanide borate, polyhexamethylene biguanide acetate, polyhexamethylene biguanide gluconate, polyhexamethylene biguanide sulfonate, polyhexamethylene biguanide maleate, polyhexamethylene biguanide ascorbate, polyhexamethylene biguanide stearate, polyhexamethylene biguanide tartrate, polyhexamethylene biguanide citrate, and combinations thereof.

8. A method for producing a lubricant composition comprising:
    contacting an alcohol selected from the group consisting of ethanol, denatured alcohol, and combinations thereof with an isocyanate-terminated prepolymer, a hydrophilic polymer other than an isocyanate-terminated prepolymer, and at least one antimicrobial agent; and
    recovering the lubricant composition.

9. The method of claim 8, wherein said isocyanate-terminated prepolymer is selected from the group consisting of polyoxyethylene-based isocyanate prepolymers, toluene diisocyanate-based prepolymers, isophorone diisocyanate-based prepolymers, hexamethylene isocyanate-terminated polyether prepolymers, and combinations thereof.

10. The method of claim 8, wherein said hydrophilic polymer is selected from the group consisting of polyvinylpyrrolidone, polyvinyl alcohol, polyacrylic acid, polyethylene oxide, and combinations thereof.

11. The method of claim 8, further comprising adding a solvent selected from the group consisting of dimethylformamide, tetrahydrofuran, methylene chloride, cyclohexanone, and combinations thereof.

12. The method of claim 8, wherein the antimicrobial agent selected from the group consisting of biguanides, biguanide salts, silver, silver salts, aminoglycosides, quinolones, penicillins, cephalosporins, and combinations thereof.

13. The method of claim 8, wherein the antimicrobial agent is selected from the group consisting of chlorhexidine, chlorhexidine acetate, chlorhexidine gluconate, chlorhexidine hydrochloride, chlorhexidine sulfate, hexamethylene biguanides, oligo-hexamethyl biguanides, silver acetate, silver benzoate, silver carbonate, silver chloride, silver iodate, silver iodide, silver lactate, silver laurate, silver nitrate, silver oxide, silver palmitate, silver protein, silver sulfadiazine, polymyxin, tetracycline, tobramycin, gentamicin, rifampician, bacitracin, neomycin, chloramphenical, miconazole, tolnaftate, oxolinic acid, norfloxacin, nalidix acid, pefloxacin, enoxacin, ciprofloxacin, ampicillin, amoxicillin, piracil, vancomycin, and combinations thereof.

14. The method of claim 8, wherein the antimicrobial agent is selected from the group consisting of polyhexamethylene biguanide, polyhexamethylene biguanide hydrochloride, polyhexamethylene biguanide hydrobromide, polyhexamethylene biguanide borate, polyhexamethylene biguanide acetate, polyhexamethylene biguanide gluconate, polyhexamethylene biguanide sulfonate, polyhexamethylene biguanide maleate, polyhexamethylene biguanide ascorbate, polyhexamethylene biguanide stearate, polyhexamethylene biguanide tartrate, polyhexamethylene biguanide citrate, and combinations thereof.

15. The method of claim 8, further comprising curing the lubricant composition.

16. A medical device at least partially coated with a lubricious composition comprising:
    an alcohol selected from the group consisting of ethanol, denatured alcohol, and combinations thereof;
    an isocyanate-terminated prepolymer;
    a hydrophilic polymer other than an isocyanate-terminated prepolymer; and
    at least one antimicrobial agent.

17. The composition of claim 16, wherein said isocyanate-terminated prepolymer is selected from the group consisting of polyoxyethylene-based isocyanate prepolymers, toluene diisocyanate-based prepolymers, isophorone diisocyanate-based prepolymers, hexamethylene isocyanate-terminated polyether prepolymers, and combinations thereof.

18. The composition of claim 16, wherein said hydrophilic polymer is selected from the group consisting of polyvinylpyrrolidone, polyvinyl alcohol, polyacrylic acid, polyethylene oxide, and combinations thereof.

19. The composition of claim 16, further comprising a solvent selected from the group consisting of dimethylformamide, tetrahydrofuran, methylene chloride, cyclohexanone, and combinations thereof.

20. The composition of claim 16, wherein the antimicrobial agent selected from the group consisting of biguanides, biguanide salts, silver, silver salts, aminoglycosides, quinolones, penicillins, cephalosporins, and combinations thereof.

21. The composition of claim 16, wherein the antimicrobial agent is selected from the group consisting of chlorhexidine, chlorhexidine acetate, chlorhexidine gluconate, chlorhexidine hydrochloride, chlorhexidine sulfate, hexamethylene biguanides, oligo-hexamethyl biguanides, silver acetate, silver benzoate, silver carbonate, silver chloride, silver iodate, silver iodide, silver lactate, silver laurate, silver nitrate, silver oxide, silver palmitate, silver protein, silver sulfadiazine, polymyxin, tetracycline, tobramycin, gentamicin, rifampician, bacitracin, neomycin, chloramphenical, miconazole, tolnaftate, oxolinic acid, norfloxacin, nalidix acid, pefloxacin, enoxacin, ciprofloxacin, ampicillin, amoxicillin, piracil, vancomycin, and combinations thereof.

22. The composition of claim 16, wherein the antimicrobial agent is selected from the group consisting of polyhexamethylene biguanide, polyhexamethylene biguanide hydrochloride, polyhexamethylene biguanide hydrobromide, polyhexamethylene biguanide borate, polyhexamethylene biguanide acetate, polyhexamethylene biguanide gluconate, polyhexamethylene biguanide sulfonate, polyhexamethylene biguanide maleate, polyhexamethylene biguanide ascorbate, polyhexamethylene biguanide stearate, polyhexamethylene biguanide tartrate, polyhexamethylene biguanide citrate, and combinations thereof.

23. The medical device of claim 16, wherein said medical device is selected from the group consisting of catheters, arterial venous shunts, gastroenteric feed tubes, endotracheal tubes, urological catheters, and wound dressings.

* * * * *